(12) United States Patent
Parker et al.

(10) Patent No.: US 9,326,874 B2
(45) Date of Patent: May 3, 2016

(54) INTRODUCER APPARATUS

(75) Inventors: Fred T. Parker, Unionville, IN (US); Palle M. Hansen, Bjaeverskov (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 937 days.

(21) Appl. No.: 13/264,329

(22) PCT Filed: Apr. 12, 2010

(86) PCT No.: PCT/US2010/030695
§ 371 (c)(1),
(2), (4) Date: Nov. 3, 2011

(87) PCT Pub. No.: WO2010/120670
PCT Pub. Date: Oct. 21, 2010

(65) Prior Publication Data
US 2012/0041537 A1 Feb. 16, 2012

Related U.S. Application Data (60) Provisional application No. 61/169,579, filed on Apr. 15, 2009.

(51) Int. Cl.
*A61F 2/966* (2013.01)
*A61F 2/95* (2013.01)
*A61F 2/97* (2013.01)

(52) U.S. Cl.
CPC . *A61F 2/966* (2013.01); *A61F 2/95* (2013.01); *A61F 2/97* (2013.01); *A61F 2002/9517* (2013.01)

(58) Field of Classification Search
CPC .............. A61F 2/95; A61F 2/97; A61F 2/966; A61F 2/962; A61F 2002/9517; A61F 2002/9665; A61F 2002/966; A61F 2002/011; A61F 2/2427; A61F 2/2436; A61F 2/243; A61F 2/2433; A61F 2/2466; A61M 2025/0034; A61M 25/0668
USPC ........................ 623/1.11, 1.12; 606/108, 198; 604/103.05, 164.05
See application file for complete search history.

(56) References Cited

U.S. PATENT DOCUMENTS 5,707,376 A * 1/1998 Kavteladze et al. ......... 623/1.11
6,287,329 B1    9/2001 Duerig et al.
(Continued)

FOREIGN PATENT DOCUMENTS

EP    1 844 739 A1    10/2007
EP    2 111 826 A1    3/2009
(Continued)

OTHER PUBLICATIONS

Search Report for related PCT Application No. PCT/US2010/030695 mailed Jun. 29, 2010.

*Primary Examiner* — Jonathan W Miles
*Assistant Examiner* — Lucas Paez
(74) *Attorney, Agent, or Firm* — Brinks Gilson & Lione (57) ABSTRACT

A stent introducer apparatus comprises a sheath for surrounding a stent member, with the sheath having a longitudinal slit extending from one end along at least a substantial part of the length thereof, and a sheath withdrawal device comprising a reel for winding up the sheath. A second sheath may surround the slit portion of the sheath. An intermediate guide member can smooth the withdrawal procedure and flatten the sheath before it is wound on the reel. The intermediate guide member may include at least one of a second reel or a slot-defining member. The reel may be operated by means of a gear system. A method of deploying a stent member is also provided.

23 Claims, 4 Drawing Sheets

(56) References Cited

U.S. PATENT DOCUMENTS

| | | |
|---|---|---|
| 6,447,540 B1 | 9/2002 | Fontaine et al. |
| 7,976,574 B2 * | 7/2011 | Papp .......................... 623/1.11 |
| 8,500,789 B2 * | 8/2013 | Wuebbeling et al. ........ 623/1.11 |
| 2002/0099431 A1 * | 7/2002 | Armstrong et al. .......... 623/1.11 |
| 2005/0033402 A1 | 2/2005 | Cully et al. |
| 2005/0080476 A1 | 4/2005 | Gunderson et al. |
| 2005/0256562 A1 * | 11/2005 | Clerc et al. ................. 623/1.11 |
| 2007/0219617 A1 * | 9/2007 | Saint .......................... 623/1.12 |
| 2007/0244540 A1 * | 10/2007 | Pryor .......................... 623/1.11 |
| 2009/0270969 A1 * | 10/2009 | Fargahi et al. .............. 623/1.11 |
| 2010/0094310 A1 * | 4/2010 | Warring et al. ............. 606/108 |

FOREIGN PATENT DOCUMENTS

| | | |
|---|---|---|
| WO | WO 2004/030571 A2 | 4/2004 |
| WO | WO 2007/013902 A2 | 2/2007 |
| WO | WO 2008/124844 A1 | 10/2008 |

\* cited by examiner

INTRODUCER APPARATUS

This application is a National Stage of International Application PCT/US2010/30695 filed Apr. 12, 2010, which claims the benefit of the filing date under 35 U.S.C. §119(e) of Provisional U.S. Patent Application Ser. No. 61/169,579, filed Apr. 15, 2009. The entirety of both applications is hereby incorporated by reference.

BACKGROUND

The presently described embodiments relate to apparatus for delivering an implantable prosthesis, in particular a stent member, to a desired location in a body of a patient.

Radially expandable prosthetic devices such as stents, stent grafts and valves may be delivered from the distal end of a catheter delivery system. The delivery system typically includes an inner catheter tube member surrounded by a sheath and extending from a proximal end controlled by an operator and a distal end inserted to a point of treatment within a body vessel. The inner catheter houses a wire guide lumen extending along at least a portion of the catheter and terminates at a tapered tip portion. The radially compressed prosthetic device may be positioned around the distal portion of the catheter between the sheath and the inner catheter member adjacent or near the distal tip. The prosthetic device is typically adapted to radially expand to an outer diameter greater than the diameter of the distal tip and inner catheter member when the prosthetic device is not radially restrained by the sheath. The sheath can be translated longitudinally with respect to the inner catheter member by the operator to permit movement of the sheath in a proximal direction, away from the tip. Movement of the sheath away from the distal tip permits the prosthetic device to radially expand away from the inner catheter member as the sheath is moved away from the radially compressed prosthetic device, deploying the prosthetic device within a body vessel. The catheter delivery system is then removed from the body vessel after deployment of the prosthetic device.

Friction between the sheath and the prosthetic device, when the sheath is translated during deployment of the prosthetic device, may hinder the steady release of the device. By requiring application of additional force by the operator, this friction may lead to sudden movement of the sheath relative to the device and/or undesirable sudden radial expansion of all or part of the device. When the outer surface of the device has a drug coating, the friction with the sheath may cause undesirable release of the drug and/or compromise drug coating uniformity. In addition, when the prosthetic device includes material that may tear or fold, such as a stent graft covering or a valve leaflet, the friction with the sheath may compromise the physical integrity of the device during the deployment procedure (e.g., causing a tear in a graft or leaflet material leading to leakage or poor performance). Friction and other deployment issues arise when the stent members are lengthier, such as greater than 100 mm. With piston-type introducers, the pushrod needs to retract at least the length of the stent, or much more for a rolling membrane, roll sock, or everted liner introducer that often require at least twice the length of the stent member for retraction.

Thus, during the deployment procedure for stent members, the need can arise to carefully remove a sheath member from a stent member and/or an inner catheter. A problem can arise in respect to long stent members in that a long handle is needed to enable longitudinal retraction of the associated sheath member.

SUMMARY

According to a first aspect, a stent introducer apparatus comprising a sheath for surrounding a stent member is provided. The sheath can have a longitudinal slit extending from one end along at least a substantial part of the length thereof. The stent introducer apparatus can also include a sheath withdrawal device comprising a reel for winding up the sheath. By providing a sheath with a longitudinal slit, the sheath withdrawal process can occur in a substantially smooth manner. This can avoid the employment of a pre-weakened line or perforations along the sheath, which still needs a force to be applied to separate the sheath along the pre-weakened line. It is then possible to avoid jerks in the withdrawal process, which could cause a deployed stent member to be undesirably displaced.

In another example, the longitudinal edges of the split in the sheath can overlap with each other. An advantage of this arrangement is that it contributes to maintaining a fluid-tight seal until the sheath is retracted when using fluid for flushing air, imaging capability, therapeutic uses, or other medical uses. In other arrangements in which the edges merely abut, there may be a risk of them moving apart before retraction, which could lead to an undesirable leak of fluid.

Alternatively, at least in regions adjacent the longitudinal slit, the sheath may be of flaccid material. An advantage of this feature is that the sheath provides low resistance to retraction and thus facilitates a smooth withdrawal. Preferably, the flaccid material comprises a fluoropolymer, and most preferably, a polytetrafluoroethylene (PTFE) or Teflon.

The stent introducer apparatus may further comprise an intermediate guide member that is arranged to be engaged with the sheath before being wound by the reel. An advantage of this feature is that the intermediate guide member serves to further enhance the smoothness of the withdrawal procedure. In one example, the intermediate guide member can include a further reel, with the sheath being arranged to touch at least part of the further reel. The further reel assists in flattening the material of the sheath as the sheath approaches the winding reel. In another example, the intermediate guide member can include a slot-defining member, with the sheath being arranged to pass through the slot-defining member. The slot-defining member is preferably a block of material, with a slot extending through the block of material from one side to another. The slot also assists in flattening the material of the sheath as the sheath approaches the winding reel.

In another example, the stent introducer apparatus further includes a control mechanism operable to rotate the reel. The control mechanism can be connected to the reel by means of a gear mechanism. The provision of a gear mechanism contributes to an easy and steady withdrawal procedure.

In another example, the stent introducer apparatus may further include a holding member and a second sheath fixed to the holding member. The second sheath can be arranged to surround at least a substantial portion of the length of the slit of the first sheath, where the second sheath is the outer sheath and the first sheath is the inner sheath. The second, outer sheath serves to protect the first, inner sheath. The reel and the intermediate guide member are mounted on the handle The stent introducer apparatus is particularly suited for use in withdrawing an everted sheath, i.e., a sheath which has been turned back on itself in the manner of a roll sock such that a double thickness of the sheath is formed.

According to a second aspect, a method of withdrawing an everted sheath from around a stent member is also provided. The everted sheath can have a longitudinal slit extending from one end along at least a substantial part of the length thereof.

The method can include winding the everted sheath on a reel, where the length of everted sheath wound on the reel substantially corresponds to at least twice the length of the stent member exposed thereby. An advantage of using this method with an everted sheath is that the extra length of the everted sheath material may be conveniently wound on the reel without potential problems due to a lack of space, which is often needed from piston type introducers. In addition, the inner surface of the everted portion of the sheath is removed from the outer surface of the stent member, or other prosthetic device, by a peeling motion rather than a sliding or shearing motion typically used in introducer apparatus. This is particular useful for longer stent members where a typical long handle is needed to enable longitudinal retraction of the associated sheath member.

The use of the intermediate guide members mentioned above is not limited to use with sheaths already having longitudinal slits. The intermediate guide members can also be used with other types of sheath including sheaths having slits or pre-weakened lines. For sheaths without slits or pre-weakened lines, the stent introducer apparatus can further include a cutter for slicing open the sheath before winding the sheath on a reel.

According to a third aspect, a stent introducer apparatus that includes a sheath for surrounding a stent member and a sheath withdrawal system having a reel for winding up the sheath is provided. The sheath withdrawal system can include an intermediate guide member arranged to be engaged by the sheath before being wound on the reel. An advantage of such an apparatus is that the stent introducer apparatus smoothes the withdrawal procedure of the sheath. The intermediate guide member can also serve to impart a flattened configuration to the sheath.

The above, as well as other advantages of the present invention, will become readily apparent to those skilled in the art from the following detailed description of a preferred embodiment when considered in the light of the accompanying drawings.

DESCRIPTION OF PREFERRED EMBODIMENTS

Figures 1, 2, 3:
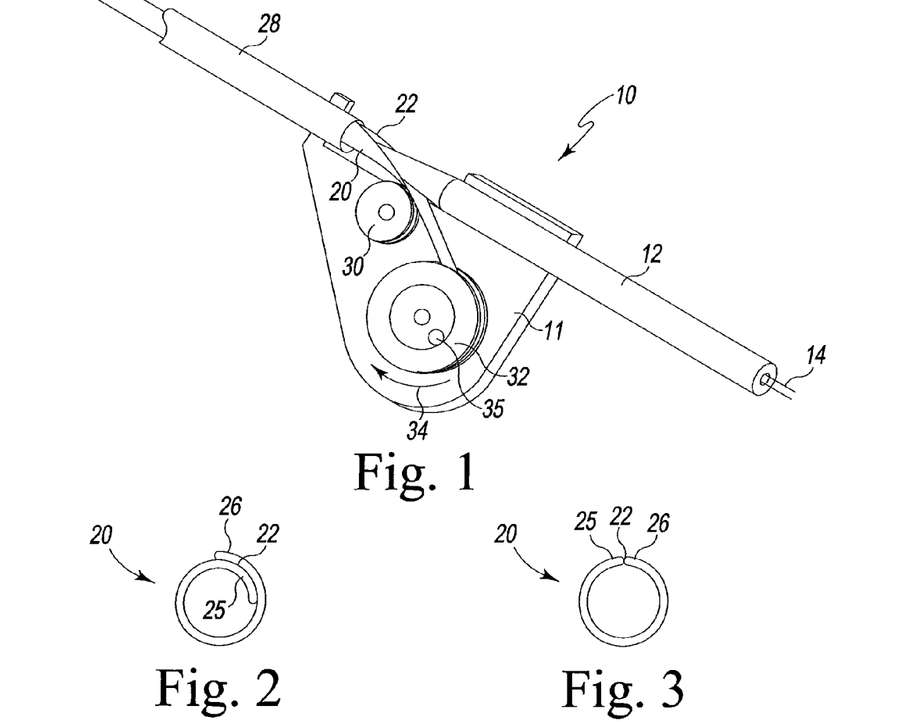
FIG. 1 is a perspective view of a stent introducer apparatus.
FIG. 2 is a cross-sectional view of one example of a sheath member of the stent introducer apparatus of FIG. 1.
FIG. 3 is a cross-sectional view similar to FIG. 1 of another example of a sheath member.

Referring to the drawings, FIG. 1 shows the proximal end of a stent introducer apparatus 10 comprising a handle part 11 which is fixedly attached to an apparatus housing (not shown). The apparatus 10 comprises a guide wire catheter or an inner catheter 12 around which is mounted a stent member (not shown) to be deployed. The stent member can be any expandable endoluminal prosthesis, such as a stent or valve prosthesis, a graft covered stent, and/or drug-coated stent. Referring to FIG. 1, the stent member is located to the left and adjacent the distal end of the stent introducer apparatus 10. The inner catheter 12 that can include a lumen to surround a guide wire 14 for guiding the apparatus to a desired location within a body vessel of a patient.

In the present specification, the term "proximal" is used for a part of the introducer apparatus which is nearer to an operator of the apparatus. The term "distal" is used for a part of the introducer apparatus which is further from an operator.

To hold the stent member in a compressed state around the inner catheter 12 during introduction, there is provided a sheath 20. As shown, sheath 20 is generally tubular with a longitudinal slit 22 that can extend from a proximal end and along most of the length of the sheath. In other examples, slit 22 is longitudinally dimensioned such that the slit extends from the proximal end to a point along the sheath, where the dimension of slit 22 is suitably sized in relation to fully deploy the stent member.

Instead of the tube having a single thickness throughout, the edges of the slit 22 can overlap, as shown in FIG. 2. The material of sheath 20 is resilient so that the overlapping edge portions 25, 26 engage firmly against each other to form a fluid-tight seal. The amount of overlap of edges 25 and 26 may vary. The edges preferably overlap by between 10% and 30% of the circumference of the tubular sheath, and most preferably by substantially 20% of the circumference. In addition, an adhesive can be applied between the overlapping edges 25, 26 to enhance sealability, but that can also be easily separated during deployment.

In the present specification, the term "sheath" is used for any tubular member or layer of a stent introducer apparatus including a catheter or liner. Moreover, two or more concentric tubular members or layers, for example, an inner sheath and an outer sheath, can be withdrawn simultaneously by the apparatus.

The proximal end of sheath 20 is surrounded by a relatively short outer sheath 28 which is fixed to the handle part 11, thus making sheath 20 an inner sheath. Also fixed to the handle part 11 can be two reels, namely a small intermediate reel 30 and a larger reel 32, which can be rotated in the direction of arrow 34 by an operator by means of a knob 35. Reel 30 serves to provide a smoother withdrawal procedure and to assist in flattening the sheath 20 as the sheath approaches reel 32.

In use of the apparatus 10, the distal end of the apparatus is carefully translated within a body vessel of a patient until the stent member is in a desired location. To deploy the stent member and allow the stent member to radially expand against the inner walls of the body vessel, sheath 20 is removed from the stent member. This can be done by passing sheath 20 over reel 30 and then around reel 32. By exerting a steady winding force on knob 35, it is then possible to wind the sheath material around reel 32 and thus retract the sheath from the stent member. As the inner sheath 20 leaves the outer sheath 28, the slit of the inner sheath opens up so that the inner sheath changes from the tubular configuration, shown in FIG. 2, to adopt a substantially flattened configuration shown in FIG. 1 that is then wound around reel 32. Once the stent member has been fully exposed, retraction of the sheath may stop, leaving some of the sheath not wound about reel 32. That is, not all of the length of sheath 20 needs to include the slit. In particular a length adjacent the distal end of the sheath 20 does not need to have a slit. The length of the nonslit portion can correspond substantially to the length left unwound after retraction is stopped. The inner catheter and the rest of the introducer apparatus 10 can then be removed from the patient, leaving only the deployed stent member behind. By virtue of the longitudinal slit, the sheath 20 may be applied to the stent member along its length in a simple operation. Thus, there is no need to roll the sheath on to the stent member from one end, which can be a complicated procedure.

An advantage of the above described arrangement is that sheath 20 can be withdrawn in one smooth and continuous winding operation without jerking and without intermittent steps that is commonly associated with pre-weakened or structurally reinforced sheaths. Only a relatively small force is needed to open up the tubular sheath at the proximal end thereof as part of the removal and winding operation. At the same time the sheath remains as fluid tight as a sheath in the form of a continuous tube without a slit. An additional advantage is that no sharp or hard edge is necessary against which to tear open the sheath 20. Thus, there is less danger of an injury to the patient or operator.

Various modifications may be made to the above described arrangement. For example the longitudinal edges 25, 26 of the slit 22 may abut as shown in FIG. 3, rather than overlap as shown in FIG. 2. Provided the material of the sheath 20 is sufficiently resilient, an adequate degree of fluid-tightness can still be maintained along the slit. Instead of being resilient, the material of the sheath 20 may be relatively flaccid. Although this may decrease the degree of fluid-tightness, the flaccid material may permit an easier and smoother withdrawal of the sheath.

Apparatus described herein may be used to withdraw a tubular sheath having a single thickness or to withdraw an everted tubular sheath having a double thickness. The everted sheath is a sheath folding in on itself that forms an exterior and interior layer of the double thickness. In one example, a rolling liner is attached between the sheath 20 and the inner catheter 12 at the distal portion of the apparatus, and the rolling liner is folded in on itself, making up the double thickness that surrounds the stent member. The layers of the rolling liner slidably interact when moving one of the layers relative to other, thereby peeling or unfolding the everted sheath from a loaded stent member. The rolling liner can evert or invert by relative longitudinal movement between the inner catheter 12 and the sheath 20. Apparatus described herein is particularly advantageous when used in connection with everted sheaths because the total length of sheath which needs to be withdrawn corresponds to at least twice the length of the stent member. For example, it will be appreciated that winding up 10 cm of sheath material exposes 5 cm of the stent member.

In some modified examples, the reel 32 has a pre-tensioned winding coil (not shown) to assist in retraction of the sheath. Means are provided for the controlled release by the operator of tension in the coil to wind up the reel 32. An advantage of this feature is that the pre-tensioning reduces the amount of force which an operator is requested to exert on the introducer apparatus 10. Accordingly, the pre-tensioning of the reel can reduce the risk of a sudden jolt to the apparatus which could cause an unwanted displacement of the stent member. The pre-tensioning of the reel can also impart a rotational speed of the reel which can be further controlled by a damper or rotational speed controller (not shown) suitably positioned in relation to the reel to control the rotational speed of the reel. One or more rotational speed controllers may be used to control the reel at one or more speeds.

Figure 4:
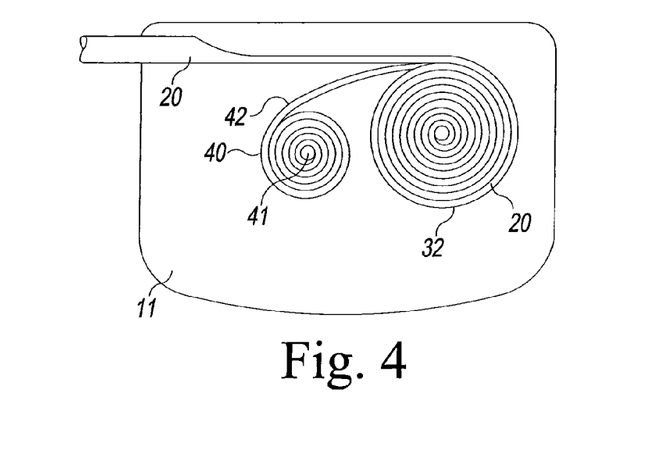
FIG. 4 is a view of a modified wind-up reel arrangement of a stent introducer apparatus.

An alternative modification to reel 32 is shown in FIG. 4. In this modification, handle 11 also carries a coil 40 of a feed stock material wound around a hub 41. The feed stock material 42 is introduced with the flattened material of sheath 20 for a mechanical advantage to more rapidly increase the outer radius of the material wound on reel 32. This results in a more rapid removal of sheath material from the stent member. Thus, for a given annular movement of reel 32, there is a greater length of the material of sheath 20 wound around the circumference of the reel with the feed stock 42. An intermediate guide member may be provided on the handle 11 upstream of the reel 32.

Figure 5:
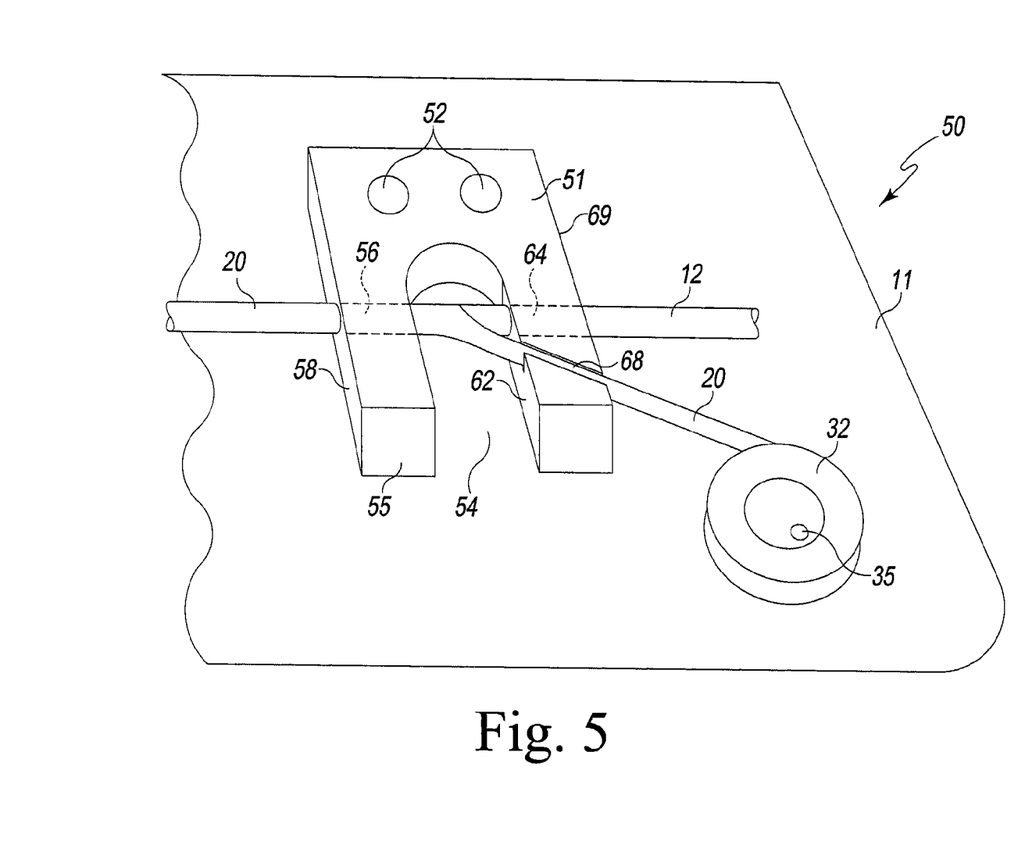
FIG. 5 is a perspective view of a portion of another stent introducer apparatus.
Figure 5A:
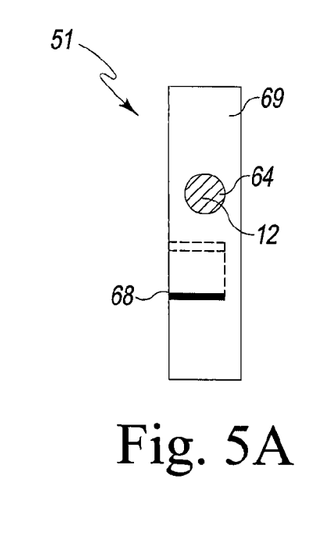
FIG. 5A is a side view of a block material in FIG. 5.

Alternative or additional means to reel 30 may be used to assist in flattening sheath 20 as the sheath approaches reel 32. FIG. 5 shows a second embodiment in which a stent introducer apparatus 50 comprises a different intermediate guide member from reel 30. Here, reel 30 is replaced by a generally cuboidal block of material 51 secured to a handle 11 by bolts 52. The block may have a recess 54, shown as U-shaped recess, in front face 55 thereof at an intermediate portion of the block. A first, substantially circular bore 56 can be provided between a side face 58 and the interior wall 62 that defines the distal edge of the recess. A second substantially circular bore 64 can be provided between wall 62 and the side face 69 of the block opposite side face 58 that defines the proximal edge of the recess. Also, extending from the mouth of the bore 64 in the recess 54 can be a groove or slot 68. The opposite end of slot 68 also can emerge from the side face 69 opposite side face 58, as shown in FIG. 5A. Slot 68 is sized to receive the sheath 20 in a substantially flattened configuration, and may not extend all the through the lateral depth of block material 51 as shown in FIG. 5A. Slot 68 may also be angularly oriented between interior wall 62 and side face 69.

In use, the sheath 20, still in substantially tubular form and still surrounding catheter 12, can pass from the outer sheath through bore 56 into recess 54. Here, sheath 20 can be stripped from catheter 12 and can be constrained to adopt a substantially flattened configuration as the sheath enters the end of slot 68 in recess 54. The sheath 20 then can pass along slot 68, emerging from the opposite end thereof and then can pass to winding reel 32. As the stripped sheath 20 passes along slot 68, the separated catheter 12 can pass along bore 64 and emerges from the side face of the block.

The block 51 thus serves to separate the sheath 20 and the catheter 12 in a carefully controlled manner. In addition, the withdrawal of the sheath 20 from the stent member can be affected without jolts and in a continuous manner.

Figure 6:
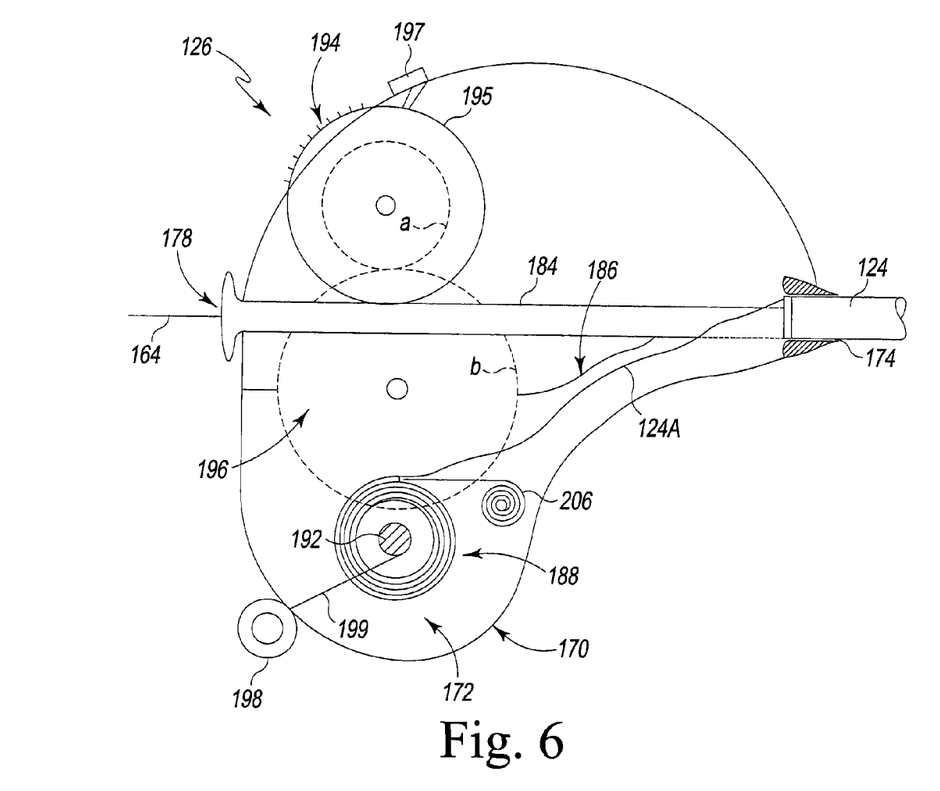
FIG. 6 is a side view of another stent introducer apparatus.
Figure 7:
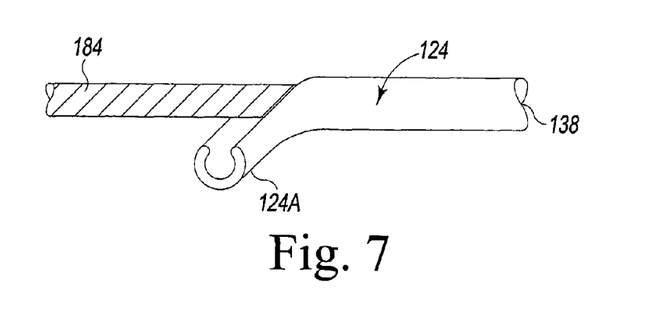
FIG. 7 is a detailed view of a portion of the stent introducer apparatus of FIG. 6.
Figure 8:
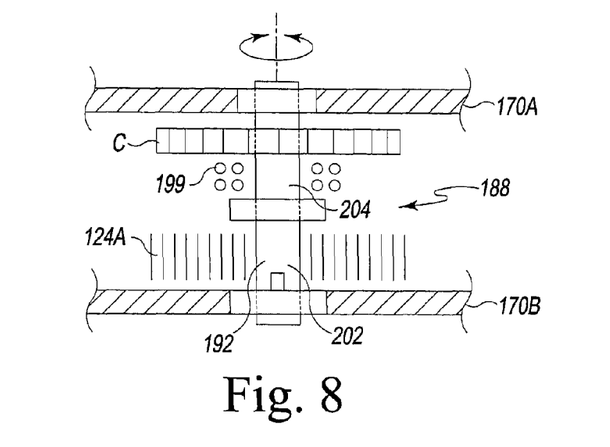
FIG. 8 is a detailed view of a spool assembly of the stent introducer apparatus of FIG. 6.

FIGS. 6-8 show the proximal end of a stent introducer apparatus in accordance with a third embodiment that may be particularly useful for deploying lengthier medical devices. The handle 126 is a multi-component assembly, ergonomically designed, which includes a housing 170 defining a cavity 172. The housing 170 is preferably a two-part molded plastic, such as ABS (acrylonitrile, butadiene, styrene), that can be snap-fit together, although the housing 170 could be molded from different polymers and/or plastics. Optionally, the handle 126 can include a port 174 for receiving a sheath 124 within the housing cavity 172. A port 178 can also be included to permit the introduction of fluid and/or a guide wire 164. For example, the port 178 illustrated is in communication with the lumen of the sheath 124.

A guiding edge 186 is configured to guide away the opened-up sheath 124A. The guiding edge may be constructed as a channel or slot in order to better flatten the sheath. FIG. 7 shows where the longitudinal slit in sheath 124 is parted to form opened-up portion 124A. A guiding member in the form of an inner catheter 184 may extend within the lumen 138 of the sheath before opening up.

The handle 126 includes a rotatable mechanism 188 having a spool assembly 192 to wind the opened-up sheath 124. The sheath can be pre-attached to the rotatable mechanism during manufacturing. The rotatable mechanism 188 can be rotatably mounted within the housing cavity 172. For example, the rotatable mechanism can be a spool or shaft that can rotate about an axle within the housing cavity. In some embodiments, the rotatable mechanism 188 is pre-tensioned to wind in order to retract the outer sheath. This can reduce the amount of force the operator must exert when retracting the sheath.

The rotatable mechanism 188 can be coupled to a control mechanism 194. The control mechanism 194 can urge the rotatable mechanism 188 to rotate in a direction suitable to retract a portion of the sheath 124 into the housing cavity 172 and to wind the opened-up portion 124A of the sheath about the spool assembly 192. The control mechanism 194 can include any number of mechanisms that can be manipulated by the operator. For example, the control mechanism 194 can be a thumbwheel, a trigger, a dial, a piston, a knob, a handle, or the like. The control mechanism 194 can be mechanically coupled to the rotatable mechanism 188 by any number of gears, pawls, ratchet wheels, sprockets, rack and pinion, or the like. For example, FIG. 6 illustrates the control mechanism 194 as a thumbwheel 195 that includes gear engaging members engageable with a gear system 196 with a series of gears a, b, c to control the rotatable mechanism 188. The gear system 196 is coupled to the gear engaging members of the thumbwheel 195 and can be rotated as the thumbwheel rotates. The gear ratio can be about 1:1 or about 1:2 or any suitable ratio known by one of ordinary skill in the art.

The handle 126 may also include a switch 197 or safety lock with a first position and a second position. The switch can operate in the first position to lock the control mechanism 194 and prevent the sheath 124 from retracting and winding. The switch 197 may also operate in the second position to enable the control mechanism 194 to operate freely, allowing a portion of the sheath 124 to retract and to wind about the rotatable mechanism 188.

A pull handle 198 may also be included in the handle 126. The pull handle permits the operator to quickly wind the reel in order to more quickly retract the sheath from the stent member or after deployment of the stent member. In one example, the pull handle 198 can be connected to the sheath 124 to retract the sheath 124. In other examples, the pull handle 198 can have a portion connected to a pull wire 199. The pull wire 199 can have a distal end attached to the rotatable mechanism 188 and a proximal end disposed external to the housing cavity 172, preferably, connected to the pull handle 198. The pull handle can be a ring, a bar, a grip handle or the like. A portion of the pull wire 199 is wound around the rotatable mechanism 188, as shown in FIG. 8. The proximal end of the pull wire 199 can be pulled to wind the opened-up portion 124A sheath and to retract the sheath 124 within the housing cavity 172.

In FIG. 8, the rotatable mechanism 188 is connected between two sides 170A, 170B of the housing. The rotatable mechanism 188 may have a first annular region 202 for receiving opened-up portion 124A sheath and a second annular region 204 adjacent to the first annular region 202, for receiving the wound pull wire 199. Preferably, the second annular region 204 is coupled to a one-way bearing. The one-way bearing can allow the winding of the sheath about the first annular region 202 without impacting or unwinding the pull wire 199 of the second annular region 204. Also shown is gear c of the gear system securably attached to the rotatable mechanism 188. It is appreciated that the shown embodiment of the rotatable mechanism 188 can be designed in various configurations, such as positioning the gear c in between the first and second annular regions 202, 204.

To increase the retraction force and speed of the sheath 124, and similar to the modification disclosed in FIG. 4, a feed stock 206 can be rotatably mounted within the housing cavity 172 and inserted with the winding of the outer sheath. Preferably, the feed stock 206 is flattened material that is wound around a second rotatable mechanism. A portion of the feed stock can be inserted with the opened-up portion 124A of the sheath while being wound about the rotatable mechanism 188. Since the feed stock is inserted between wound portions of the sheath, the distance from the center to the edge of the wound portion of the sheath increases more rapidly for a mechanical advantage. Thus, for a given annular movement of the rotatable mechanism there is greater length of the sheath that will wind around the rotatable mechanism. The thickness of the feed stock can be uniform, such as 0.01 inches, or can be tapered or stepped at a suitable rate. The rate of tapering can be uniform, for example 0.01 inches per the circumference distance of the rotatable mechanism, or can vary as required to increase the retraction rate at the desired rate.

The use of gear system 196 further contributes to a smooth and steady release of a prosthetic device. An intermediate member (not shown in FIG. 6), such as reel 30 shown in FIG. 1 or block 51 shown in FIG. 5, may also be included to provide a smoother withdrawal procedure and to assist in flattening the sheath as the sheath approaches the winding reel.

Drawings in the figures illustrating various embodiments are not necessarily to scale. Some drawings may have certain details magnified for emphasis, and any different numbers or proportions of parts should not be read as limiting, unless so-designated in the present disclosure. Those skilled in the art will appreciate that embodiments not expressly illustrated herein may be practiced within the scope of the present invention, including those features described herein for different embodiments may be combined with each other and/or with currently-known or future-developed technologies while remaining within the scope of the claims presented here. In other words, the features of the various embodiments and modifications described may be interchanged or combined as desired. It is therefore intended that the foregoing detailed description be regarded as illustrative rather than limiting. And, it should be understood that the following claims, including all equivalents, are intended to define the spirit and scope of this invention.

The invention claimed is:

1. A stent introducer apparatus comprising a sheath configured to surround a stent member, the sheath having a longitudinal slit extending from one end along at least a portion of the length thereof, an inner catheter extending through the sheath, a sheath withdrawal device comprising a reel configured to wind up the sheath, wherein the sheath is stripped from the inner catheter to form a stripped portion of the sheath, the stripped portion wound onto the sheath withdrawal device, and an intermediate guide member arranged between the inner catheter and the sheath withdrawal device, the intermediate guide member being engaged by the stripped portion before the stripped portion is wound on said reel, and after the stripped portion is stripped from the inner catheter, wherein said intermediate guide member is a further reel.

2. An apparatus according to claim 1 further comprising a holding member and a second sheath fixed to the holding member, the second sheath being arranged to surround the slit length of the first sheath.

3. An apparatus according to claim 1 wherein a pre-tensioned coil is provided to wind up said reel.

4. An apparatus according to claim 1 comprising a control mechanism operable to rotate said reel, said control mechanism being connected to said reel by means of a gear mechanism.

5. A stent introducer apparatus comprising a sheath configured to surround a stent member, the sheath having a longitudinal slit extending from one end along at least a portion of the length thereof, an inner catheter extending through the sheath, a sheath withdrawal device comprising a reel configured to wind up the sheath, wherein the sheath is stripped from the inner catheter to form a stripped portion of the sheath, the stripped portion wound onto the sheath withdrawal device, and an intermediate guide member arranged between the inner catheter and the sheath withdrawal device, the intermediate guide member being engaged by the stripped portion before the stripped portion is wound on said reel, and after the stripped portion is stripped from the inner catheter, wherein said intermediate guide member comprises a slot-defining member, the stripped portion being arranged to pass through said slot.

6. An apparatus according to claim 5 wherein the slit is longitudinally dimensioned such that the slit extends distally to a point along the sheath, a proximal portion of the sheath thereby being slit and a distal portion of the sheath being nonslit.

7. An apparatus according to claim 5 wherein said slot-defining member is a block of material and said slot extends through said block from one side to another.

8. An apparatus according to claim 7 wherein said block comprises a recess in an intermediate portion thereof to expose the stripped portion of the sheath.

9. An apparatus according to claim 8 wherein said block includes a portion defining a proximal edge of the recess, said slot extending through said portion and dimensioned to receive said stripped portion of the sheath in a flattened configuration.

10. An apparatus according to claim 1 wherein longitudinal edges of the slit in the sheath overlap each other.

11. An apparatus according to claim 10 wherein the sheath, at least in regions adjacent the longitudinal slit, is of resilient material.

12. An apparatus according to claim 10 wherein the sheath, at least in regions adjacent the longitudinal slit, is of flaccid material.

13. An apparatus according to claim 1 wherein the slit is longitudinally dimensioned such that the slit extends distally to a point along the sheath, a proximal portion of the sheath thereby being slit and a distal portion of the sheath being nonslit.

14. An apparatus according to claim 1 wherein a length of the slit is at least twice a length of the stent member.

15. A stent introducer apparatus comprising a sheath configured to surround a stent member, the sheath having a longitudinal slit extending from one end along at least a portion of the length thereof, an inner catheter extending through the sheath, a sheath withdrawal device comprising a reel configured to wind up the sheath, wherein the sheath is stripped from the inner catheter to form a stripped portion of the sheath, the stripped portion wound onto the sheath withdrawal device, and an intermediate guide member arranged between the inner catheter and the sheath withdrawal device, the intermediate guide member being engaged by the stripped portion before the stripped portion is wound on said reel, and after the stripped portion is stripped from the inner catheter, and a supply of feed stock material and means for winding the sheath and the feed stock material on said reel together.

16. An apparatus according to claim 15 wherein a length of the slit is at least twice a length of the stent member.

17. A method of withdrawing an everted sheath from around a stent member and an inner catheter extending through the sheath, the sheath having a longitudinal slit extending from one end along at least a part of the length thereof, the method comprising stripping the sheath from the inner catheter to form a stripped portion of the sheath by winding the stripped portion on a reel, wherein the length of sheath wound on the reel substantially corresponds to twice the length of the stent member exposed thereby, and passing the stripped portion through an intermediate guide after the stripped portion is stripped from the inner catheter and before the stripped portion is wound on the reel, the intermediate guide member comprising a slot, the intermediate guide member being disposed between the inner catheter and the sheath withdrawal device.

18. A method according to claim 17 further comprising flattening the stripped portion with the slot between withdrawal from the stent member and winding on said reel.

19. A method according to claim 17 further comprising overlapping portions of the sheath defined by the slit.

20. A method according to claim 17 further comprising providing a second sheath, and surrounding the slit portion of said sheath with the second sheath.

21. A stent introducer apparatus comprising:
a sheath configured to surround a stent member,
a sheath withdrawal system comprising a reel configured to wind up the sheath,
an inner catheter extending through the sheath, wherein the sheath is stripped from the inner catheter to form a stripped portion of the sheath, the stripped portion wound onto the sheath withdrawal device, and
an intermediate guide member arranged between the inner catheter and the sheath withdrawal device, the intermediate guide member being engaged by the stripped portion before the stripped portion is wound on said reel, and after the stripped portion is stripped from the inner catheter,
wherein said intermediate guide member is a further reel.

22. A stent introducer apparatus comprising:
a sheath configured to surround a stent member,
a sheath withdrawal system comprising a reel configured to wind up the sheath,
an inner catheter extending through the sheath, wherein the sheath is stripped from the inner catheter to form a stripped portion of the sheath, the stripped portion wound onto the sheath withdrawal device, and
an intermediate guide member arranged between the inner catheter and the sheath withdrawal device, the intermediate guide member being engaged by the stripped portion before being wound on said reel and after the stripped portion is stripped from the inner catheter,
wherein said intermediate guide member comprises a slot-defining member, the stripped portion being arranged to pass through said slot.

23. An apparatus according to claim 22 wherein said slot-defining member is a block of material and said slot extends through said block from one side to another.

* * * * *